(12) United States Patent
Park

(10) Patent No.: US 12,042,375 B2
(45) Date of Patent: Jul. 23, 2024

(54) NEGATIVE POISSON'S RATIO MATERIALS FOR INTRAOCULAR LENSES

(71) Applicant: Joon Bu Park, Huntington Beach, CA (US)

(72) Inventor: Joon Bu Park, Huntington Beach, CA (US)

(*) Notice: Subject to any disclaimer, the term of this patent is extended or adjusted under 35 U.S.C. 154(b) by 0 days.

(21) Appl. No.: 17/527,830

(22) Filed: Nov. 16, 2021

(65) Prior Publication Data
US 2023/0149153 A1    May 18, 2023

(51) Int. Cl.
*A61F 2/16* (2006.01)
*A61F 2/14* (2006.01)

(52) U.S. Cl.
CPC .......... *A61F 2/1613* (2013.01); *A61F 2/1453* (2015.04); *A61F 2002/1682* (2015.04); *A61F 2002/1689* (2013.01); *A61F 2220/0091* (2013.01); *A61F 2230/0006* (2013.01); *A61F 2230/0052* (2013.01); *A61F 2250/0018* (2013.01); *A61F 2250/0091* (2013.01)

(58) Field of Classification Search
CPC .............. A61F 2/1613; A61F 2/1453; A61F 2002/1682; A61F 2002/1689; A61F 2220/0091; A61F 2230/0006; A61F 2230/0052; A61F 2250/0018; A61F 2250/0091; A61F 2/16; A61F 2/1635
See application file for complete search history.

(56) References Cited

U.S. PATENT DOCUMENTS

| | | | |
|---|---|---|---|
| 4,834,750 A * | 5/1989 | Gupta | A61F 2/16 623/6.58 |
| 5,628,798 A | 5/1997 | Eggleston et al. | |
| 6,013,101 A * | 1/2000 | Israel | A61F 2/1629 623/6.43 |
| 8,216,310 B2 * | 7/2012 | Hu | C08G 77/70 623/6.46 |
| 2005/0021139 A1 * | 1/2005 | Shadduck | A61F 2/1694 623/6.37 |

(Continued)

FOREIGN PATENT DOCUMENTS

WO    WO-9007575 A * 7/1990 ............... A61F 2/15

OTHER PUBLICATIONS

Chaobo Song, Shuang Li, Jiapeng Zhang, Zhenhao Xi, Eryi Lu, Ling Zhao, Lian Cen, Controllable fabrication of porous PLGA/PCL bilayer membrane for GTR using supercritical carbon dioxide foaming,2019,Applied Surface Science, vol. 472, pp. 82-92, https://doi.org/10.1016/j.apsusc.2018.04.059. (Year: 2019).*

(Continued)

*Primary Examiner* — Melanie R Tyson
*Assistant Examiner* — Yasniary De La Caridad Morales
(74) *Attorney, Agent, or Firm* — Fish & Richardson P.C.

(57) ABSTRACT

An intraocular lens includes a substantially circular lens element formed of a transparent material and one or more haptics extending outwardly from an outer edge of the lens element. The one or more haptics are formed of a polymer foam material having a negative Poisson's ratio (NPR) and are configured to couple the intraocular lens to an eye of a patient. The lens includes an inner region having a first index of refraction and an outer region disposed circumferentially surrounding the inner region, the outer region having a second index of refraction different from the first index of refraction.

18 Claims, 12 Drawing Sheets

(56) References Cited

U.S. PATENT DOCUMENTS

2005/0277864 A1* 12/2005 Haffner ............... A61F 9/00781
  604/8
2006/0116765 A1*  6/2006 Blake ................... A61F 2/1618
  623/6.46

OTHER PUBLICATIONS

Bhushan B, Burton Z. Adhesion and friction properties of polymers in microfluidic devices. (2005) Nanotechnology.;16:467-78. pp. 466-47, DOI 10.1088/0957-4484/16/4/023 (Year: 2005).*
PCT International Search Report and Written Opinion in International Appln. No. PCT/US22/49948, dated Feb. 22, 2023, 9 pages.

* cited by examiner

NEGATIVE POISSON'S RATIO MATERIALS FOR INTRAOCULAR LENSES

BACKGROUND

The present disclosure relates generally to materials for intraocular lenses. An intraocular lens is a device that is surgically placed in an eye, e.g., to replace or supplement the focusing power of a natural lens.

SUMMARY

We describe here intraocular lenses that include materials having a negative Poisson's ratio ("NPR materials").

In an aspect, the intraocular lens includes a substantially circular lens element formed of a transparent material and one or more haptics extending outwardly from an outer edge of the lens element, the one or more haptics formed of a polymer foam material having a negative Poisson's ratio (NPR), in which the one or more haptics are configured to couple the intraocular lens to an eye of a patient. The lens includes an inner region having a first index of refraction and an outer region disposed circumferentially surrounding the inner region, the outer region having a second index of refraction different from the first index of refraction.

Embodiments of the intraocular lens can include one or any combination of two or more of the following features. The outer region of the intraocular lens element is formed of a polymer foam NPR material. The inner region of the intraocular lens element is formed of acrylic (e.g., polymethylmethacrylate), silicone, or hydrogel. The intraocular lens includes two haptics disposed at diametrically opposed positions around a circumference of the lens element. The intraocular lens element includes four haptics disposed at evenly spaced intervals around a circumference of the lens element. The haptics include one or more loop haptics. The haptics include one or more plate loop haptics. The haptics include one or more solid plate haptics. The haptics include one or more T-shaped haptics. The width of each haptic is less than the diameter of the lens element. The width of each haptic is substantially equal to a diameter of the lens element. One or more haptics include a hinge attaching the haptic to the lens element. The hinge attaching the haptic to the lens element includes grooves in the haptic. The lens element is convex. The polymer foam material of the lens element is composed of a cellular structure having a characteristic dimension of between 0.1 μm and 3 μm. The polymer foam material includes a foam of acrylic (e.g., polymethylmethacrylate), silicone, or hydrogel.

In an aspect, a method of implanting an intraocular lens in an eye of a patient includes creating an incision in a cornea of the eye of the patient, inserting the intraocular lens into the eye of the patient through the incision in the cornea, and securing the intraocular lens in the eye such that a substantially circular, transparent lens element of the intraocular lens is disposed along an optical axis of the eye and one or more haptics of the intraocular lens are in contact with tissue of the eye, in which the one or more haptics are formed of a polymer foam material having a negative Poisson's ratio.

Embodiments of the method of implanting an intraocular lens in an eye of a patient can include one or any combination of two or more of the following features. The existing lens is removed from the eye of the patient prior to inserting the intraocular lens. The intraocular lens is inserted into a posterior chamber of the eye. The intraocular lens is inserted into an anterior chamber of the eye.

Other implementations are within the scope of the claims.

DETAILED DESCRIPTION

Figure 1:
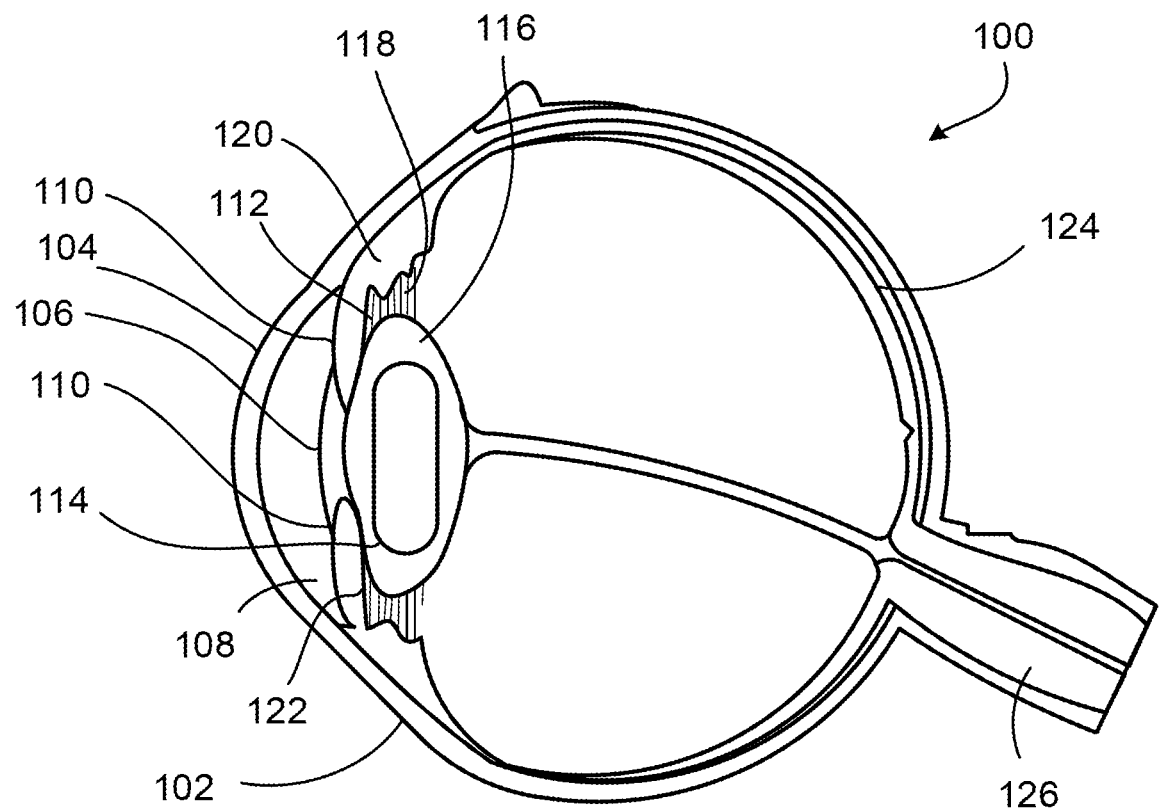
FIG. 1 is an illustration of components of the human eye.

This disclosure describes intraocular lenses (IOLs) formed in part from materials having a negative Poisson's ratio ("NPR materials"). An intraocular lens is a device that is surgically placed in an eye, e.g., to replace or supplement the focusing power of a natural lens, e.g., if the natural lens becomes clouded by cataracts, damaged, or lacks sufficient focusing power. The inclusion of NPR materials in intraocular lenses can produce intraocular lenses which are lighter, more comfortable and easier to implant than lenses made with conventional materials (e.g., materials having a positive Poisson's ratio ("PPR materials"). Surgical procedures used to place an IOL within the eye of a patient are also described in this disclosure.

The IOL 200 can be fabricated as a single-piece or a multi-piece lens. All components of a single piece lens are manufactured from the same material. A multi-piece lens can have the optical zone 204 of the optic 202, the circumferential optic 206 of the optic, and the haptics 208 fabricated from different materials. The circumferential optic 206, which provides a point of attachment for the haptics 208, can be made of a different material than either the haptics 208 or the optical zone 204 of the intraocular lens. The disclosure describes the use of a negative Poisson's ratio (NPR) material for the haptics 208, the circumferential optic 206, or both, in an intraocular lens 200.

Approximately two-thirds of the focusing power of the eye is achieved by the cornea 104. The remaining approximately one-third of the focusing power is achieved by the lens 114. Unlike the cornea 104, which remains static as it refracts light, the action of the ciliary body muscles 120 allows the lens 114 to dynamically change in order to vary the distance at which the eye can focus an image: the lens 114 can become thicker to focus on nearby objects and thinner to focus on distant objects. After being refracted through the lens, the fully focused light impinges on a retina 124, is converted to neural signals, and is transmitted to the brain for image formation by an optic nerve 126.

As humans age, the lens 114 can stiffen and lose the flexibility which allows the eye to focus on objects over the full range of distances. Proteins in the lens can break down over time, leaving the lens cloudy and impeding its ability to transmit and focus light. These protein deposits, called cataracts, may become so severe that the removal and replacement of the lens becomes appropriate. An intraocular lens is a device that is surgically placed in the eye, e.g., to replace or supplement the focusing power of the natural lens 114, e.g., if the natural lens becomes clouded by cataracts, damaged, or lacks sufficient focusing power. An IOL may be implanted into the eye following removal of the natural lens 114, or may be placed over the existing natural lens 114 to change the focusing power of the eye. Examples of conditions that may be treated by the replacement of the lens of the eye with an intraocular lens or the insertion of an IOL over the lens include hyperopia, myopia, presbyopia, astigmatism, eye trauma, and genetic eye conditions.

The anterior and posterior surfaces of an intraocular lens (IOL) each has a radius of curvature designed to refract light. Each of the two surfaces can be flat (with a radius of curvature equal to infinity) or convex (with a radius of curvature greater than zero and less than infinity). A convex surface can have a radius of curvature that is set depending on the function of the lens. In some lenses, the radius of curvature of the anterior surface differs from the radius of curvature of the posterior surface of the lens. Biconvex lenses have two convex surfaces with different radii of curvature for the surfaces. Equiconvex lenses have two convex surfaces with the same radius of curvature for both surfaces. Planoconvex lenses have one flat surface and one convex surface. The aperture of these refracting surfaces defines the optical zone of the IOL.

Intraocular lenses include four general functional types: monofocal, toric, presbyopic-correction, and phakic. Monofocal IOLs can be used to correct vision at a single distance range, and these lenses can be configured to correct either nearsightedness or farsightedness. Toric IOLs can be used for patients who have corneal astigmatism. Toric IOLs have markers on the peripheral parts of the lens that enable the surgeon to see the orientation of the astigmatism correction in the lens. Once the toric IOL is implanted in the eye, the surgeon then rotates the lens so the astigmatism correction is properly aligned for best results. Monofocal or toric IOLs generally correct only one type of visual deficiency. Presbyopic-correcting IOLs can be used to correct multiple vision deficiencies and include the following general functional types: multifocal IOLs which provide multiple zones of lens power that produce more than one focal point; bifocal diffractive IOLs which create two distinct images at near and far distant ranges; trifocal diffractive IOLs which improve intermediate vision compared to bifocal IOLs by providing a third range of focus; refractive IOLs which create multiple focal points that allow viewing at all distances; extended depth of focus IOLs which are designed to give an elongated focus of vision without compromising distance visual acuity; accommodative IOLs which simulates the natural accommodative process in the eye by changing power in response to ciliary muscle contraction. A phakic IOL is placed over the existing natural lens and is used to change the eye's focusing power.

Figure 2:
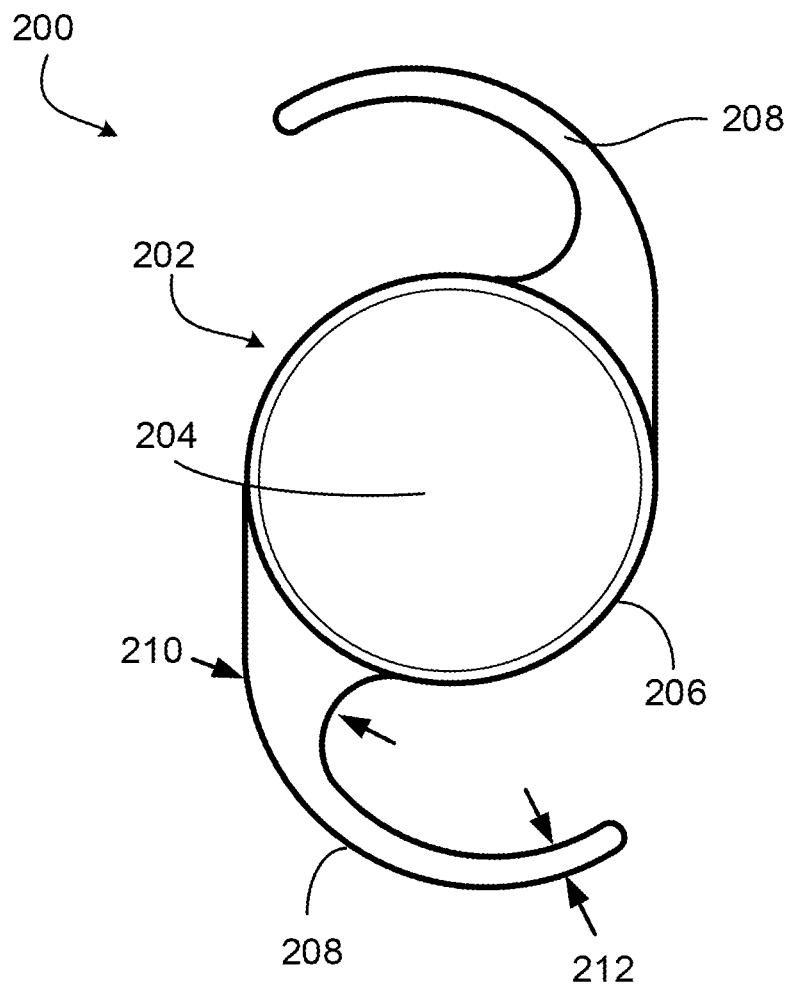
FIG. 2 is one embodiment of two-loop intraocular lens.

A two-loop embodiment of an intraocular lens 200 is shown in FIG. 2. A central, substantially circular portion of the intraocular lens 200 is called an optic 202. A region of the optic 202 which focuses the light is called an optical zone 204. The optical zone 204 is a rounded (e.g., generally circular) region in an interior of the optic 202. The optical zone 204 has a first index of refraction that, when the IOL 200 is implanted in an eye, facilitates focusing of light. The shape, curvature, or both of the optical zone 204 can facilitate focusing of light. The optic 202 includes a circumferential optic 206 concentrically surrounding the outer circumference of the optical zone 204. The circumferential optic 206 can be made of a different material than the optical zone and can have a second index of refraction different from the first index of refraction.

Haptics 208 extend outwardly from the outer edge of the optic 202. The haptics are flexible extensions that help to stabilize and center the lens within the eye after implantation. The haptics can be attached to the optic 202 at the circumferential optic 206. The IOL depicted in FIG. 2 is a two-loop intraocular lens 200 with two loop haptics 208 at diametrically opposed positions around the circumferential optic 206. Each haptic 208 decreases in width with increasing distance from the optic, from an inner width 210 to an outer width 212, with the outer width 212 less than the inner width 210. Both the inner width 210 and the outer width 212 are significantly less than a diameter of the optic 202.

The optical zone 204 can be formed from a transparent material, e.g., a transparent polymer material, having a positive Poisson's ratio (PPR) with a first index of refraction. The material used to form the optical zone can include acrylic (e.g., polymethyl methacrylate (PMMA)), polycarbonate, silicone, or hydrogel, or a combination thereof. One or more of the haptics 208, the circumferential optic 206, or all of them can be formed of a material having a negative Poisson's ration (NPR), e.g., an NPR foam material, such as an NPR polymer foam material or an NPR polymer sponge material. In some examples, the circumferential optic 206 and both haptics 208 are made from the same NPR material. In some examples, the circumferential optic 206 is made from one NPR material, and the haptics 208 are made from a different NPR material. In some examples, the circumferential optic 206 and each haptic 208 is each made from a different NPR material.

FIG. 1 shows a schematic of a human eye 100. A sclera 102 is the white outermost layer of the eye that covers and maintains the shape of the eye. A cornea 104 is on the front, exterior of the eye and is made of transparent tissue that acts to refract light entering a pupil 106. An anterior chamber 108 is a fluid-filled cavity in the front part of the eye between the cornea 104 and an iris 110. The iris 110 controls the amount of light that enters the eye by controlling the diameter of the pupil 106. A posterior chamber 112 is a fluid-filled cavity between a lens 114 and the iris 110. A capsular bag 116 is a structure that holds the lens 114 in a central position within the eye. Attached to the lens 114 are small suspensory ligaments (zonules) 118 extending from the inner wall of the eye that connect to a ciliary body 120. The ciliary body 120 is the middle layer of the wall of the eye and includes a ring-shaped muscle. A ciliary sulcus 122 is a small space between the posterior surface of the iris 110 and the anterior surface the ciliary body 120. The lens 114 is elastic and can change its shape when pulled on by the ciliary body muscles 120.

Properties that may be important for materials used for intraocular lenses include biocompatibility, infection resistance, clarity, refractive index, durability, flexibility, UV filtration, or any combination of these properties. Materials generally undergo quality control to ensure they meet criteria appropriate to be used for IOLs. Although polymethylmethacrylate (PMMA) was used extensively for early versions of IOLs and is still in use today, other polymer materials also have been implemented in IOLs. Examples of materials that are used to fabricate intraocular lenses include acrylics, silicone, polycarbonate, or combinations thereof. Acrylic materials can be rigid (e.g., PMMA) or flexible. The acrylic materials can be either hydrophobic or hydrophilic. Hydrogels, which include hydrophilic polymers of acrylic and silicone, also can be used to fabricate IOLs. The disclosure describes the use of a negative Poisson's ratio (NPR) material for the haptics 208, the circumferential optic 206 of the optic 202, or both, in an intraocular lens. NPR materials used in IOLs can be selected to have properties suitable for use in intraocular lenses. For instance, the haptics 208, the circumferential optic 206, or both can incorporate NPR materials of acrylics (e.g., PMMA), silicone, polycarbonate, or hydrogels.

An NPR material is a material that has a Poisson's ratio that is less than zero, such that when the material experiences a positive strain along one axis (e.g., when the material is stretched), the strain in the material along the two perpendicular axes is also positive (e.g., the material expands in cross-section). Conversely, when the material experiences a negative strain along one axis (e.g., when the material is compressed), the strain in the material along a perpendicular axis is also negative (e.g., the material compresses along the perpendicular axis). By contrast, a material with a positive Poisson's ratio (a "PPR material") has a Poisson's ratio that is greater than zero. When a PPR material experiences a positive strain along one axis (e.g., when the material is stretched), the strain in the material along the two perpendicular axes is negative (e.g., the material compresses in cross-section), and vice versa.

Figure 3:
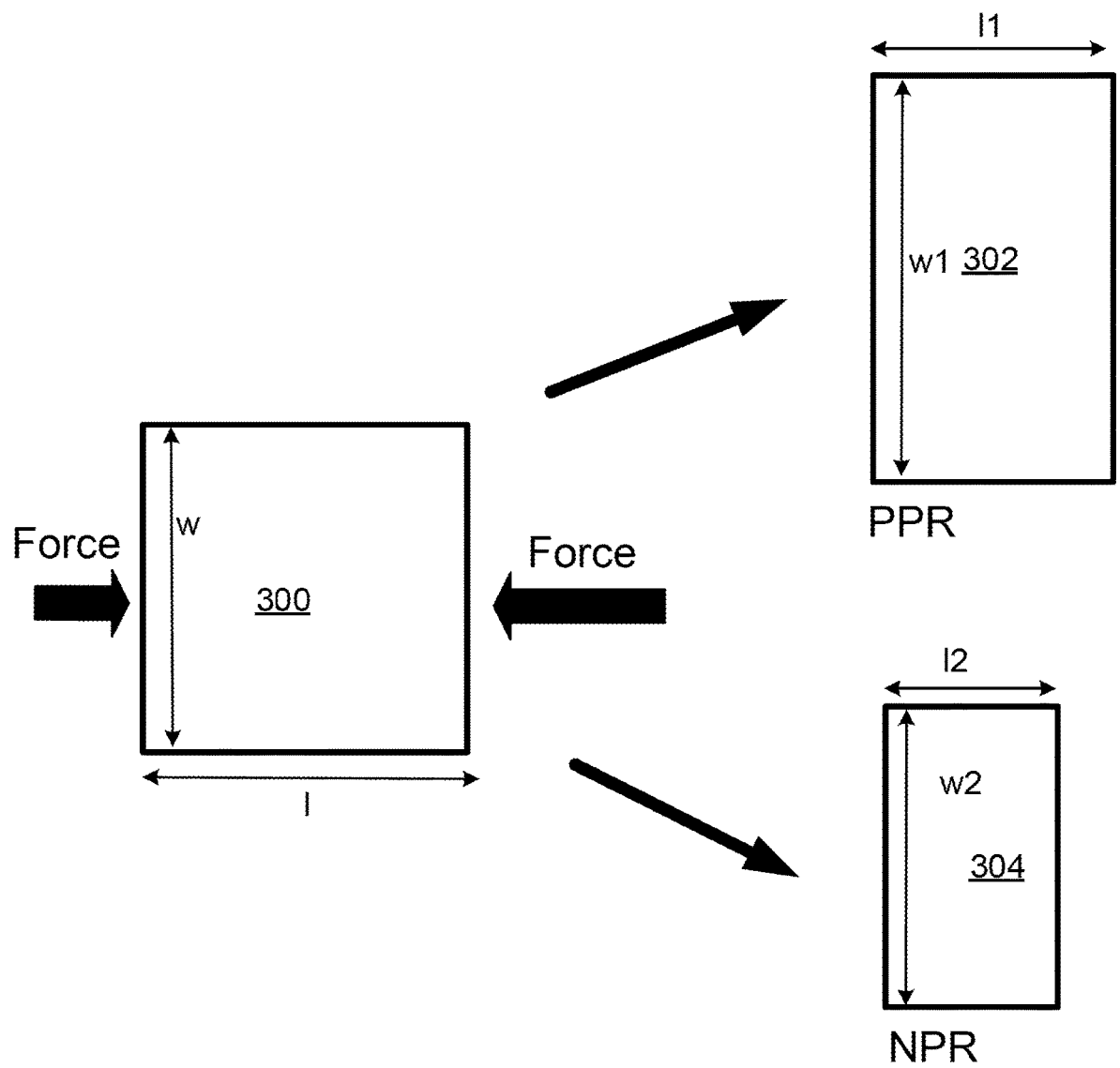
FIG. 3 is an illustration of materials with negative and positive Poisson's ratios.

Materials with negative and positive Poisson's ratios are illustrated in FIG. 3, which depicts a hypothetical two-dimensional block of material 300 with length l and width w.

If the hypothetical block of material 300 is a PPR material, when the block of material 300 is compressed along its width w, the material deforms into the shape shown as block 302. The width w1 of block 302 is less than the width w of block 300, and the length l1 of block 302 is greater than the length l of block 300: the material compresses along its width and expands along its length.

By contrast, if the hypothetical block of material 300 is an NPR material, when the block of material 300 is compressed along its width w, the material deforms into the shape shown as block 304. Both the width w2 and the length l2 of block 304 are less than the width w and length l, respectively, of block 300: the material compresses along both its width and its length.

NPR materials intraocular lenses can be foams, such as polymeric foams, ceramic foams, metal foams, or combinations thereof. A foam is a multi-phase composite material in which one phase is gaseous and the one or more other phases are solid (e.g., polymeric, ceramic, or metal). Foams can be closed-cell foams, in which each gaseous cell is sealed by solid material; open-cell foams, in which each cell communicates with the outside atmosphere; or mixed, in which some cells are closed and some cells are open.

An example of an NPR foam structure is a re-entrant structure, which is a foam in which the walls of the cells are concave, e.g., protruding inwards toward the interior of the cells. In a re-entrant foam, compression applied to opposing walls of a cell will cause the four other, inwardly directed walls of the cell to buckle inward further, causing the material in cross-section to compress, such that a compression occurs in all directions. Similarly, tension applied to opposing walls of a cell will cause the four inwardly directed walls of the cell to unfold, causing the material in cross-section to expand, such that expansion occurs in all directions. NPR foams can have a Poisson's ratio of between −1 and 0, e.g., between −0.8 and 0, e.g., −0.8, −0.7, −0.6, −0.5, −0.4, −0.3, −0.2, or −0.1. NPR foams can have an isotropic Poisson's ratio (e.g., Poisson's ratio is the same in all directions) or an anisotropic Poisson's ratio (e.g., Poisson's ratio when the foam is strained in one direction differs from Poisson's ratio when the foam is strained in a different direction).

An NPR foam can be polydisperse (e.g., the cells of the foam are not all of the same size) and disordered (e.g., the cells of the foam are randomly arranged, as opposed to being arranged in a regular lattice). An NPR foam can have a characteristic dimension (e.g., the size of a representative cell, such as the width of the cell from one wall to the opposing wall) ranging from 0.1 µm to about 3 mm, e.g., about 0.1 µm, about 0.5 µm, about 1 µm, about 10 µm, about 50 µm, about 100 µm, about 500 µm, about 1 mm, about 2 mm, or about 3 mm.

In some examples, NPR foams are produced by transformation of PPR foams to change the structure of the foam into a structure that exhibits a negative Poisson's ratio. In some examples, NPR foams are produced by transformation of nanostructured or microstructured PPR materials, such as nanospheres, microspheres, nanotubes, microtubes, or other nano- or micro-structured materials, into a foam structure that exhibits a negative Poisson's ratio. The transformation of a PPR foam or a nanostructured or microstructured material into an NPR foam can involve thermal treatment (e.g., heating, cooling, or both), application of pressure, or a combination thereof. In some examples, PPR materials, such as PPR foams or nanostructured or microstructured PPR materials, are transformed into NPR materials by chemical processes, e.g., by using glue. In some examples, NPR materials are fabricated using micromachining or lithographic techniques, e.g., by laser micromachining or lithographic patterning of thin layers of material. In some examples, NPR materials are fabricated by additive manufacturing (e.g., three-dimensional (3D) printing) techniques, such as stereolithography, selective laser sintering, or other appropriate additive manufacturing technique.

In an example, a PPR thermoplastic foam, such as an elastomeric silicone film, can be transformed into an NPR foam by compressing the PPR foam, heating the compressed foam to a temperature above its softening point, and cooling the compressed foam. In an example, a PPR foam composed of a ductile metal can be transformed into an NPR foam by uniaxially compressing the PPR foam until the foam yields, followed by uniaxially compression in other directions.

In some examples, NPR foams are produced by transformation of PPR foams to change the structure of the foam into a structure that exhibits a negative Poisson's ratio. In some examples, NPR foams are produced by transformation of nanostructured or microstructured PPR materials, such as nanospheres, microspheres, nanotubes, microtubes, or other nano- or micro-structured materials, into a foam structure that exhibits a negative Poisson's ratio. The transformation of a PPR foam or a nanostructured or microstructured material into an NPR foam can involve thermal treatment (e.g., heating, cooling, or both), application of pressure, or a combination thereof. In some examples, PPR materials, such as PPR foams or nanostructured or microstructured PPR materials, are transformed into NPR materials by chemical processes, e.g., by using glue. In some examples, NPR materials are fabricated using micromachining or lithographic techniques, e.g., by laser micromachining or lithographic patterning of thin layers of material. In some examples, NPR materials are fabricated by additive manufacturing (e.g., three-dimensional (3D) printing) techniques, such as stereolithography, selective laser sintering, or other appropriate additive manufacturing technique.

In an example, a PPR thermoplastic foam, such as an elastomeric silicone film, can be transformed into an NPR foam by compressing the PPR foam, heating the compressed foam to a temperature above its softening point, and cooling the compressed foam. Transformation processes can be done inside a predetermined dimension. In an example, a PPR foam composed of a ductile metal can be transformed into an NPR foam by uniaxially compressing the PPR foam until the foam yields, followed by uniaxially compression in other directions.

NPR-PPR composite materials are composites that include both regions of NPR material and regions of PPR material. NPR-PPR composite materials can be laminar composites, matrix composites (e.g., metal matrix composites, polymer matrix composites, or ceramic matrix composites), particulate reinforced composites, fiber reinforced composites, or other types of composite materials. In some examples, the NPR material is the matrix phase of the composite and the PPR material is the reinforcement phase, e.g., the particulate phase or fiber phase. In some examples, the PPR material is the matrix phase of the composite and the NPR material is the reinforcement phase.

NPR materials can exhibit various desirable properties, including high shear modulus, effective energy absorption, and high toughness (e.g., high resistance to indentation, high fracture toughness), among others.

Figure 4:
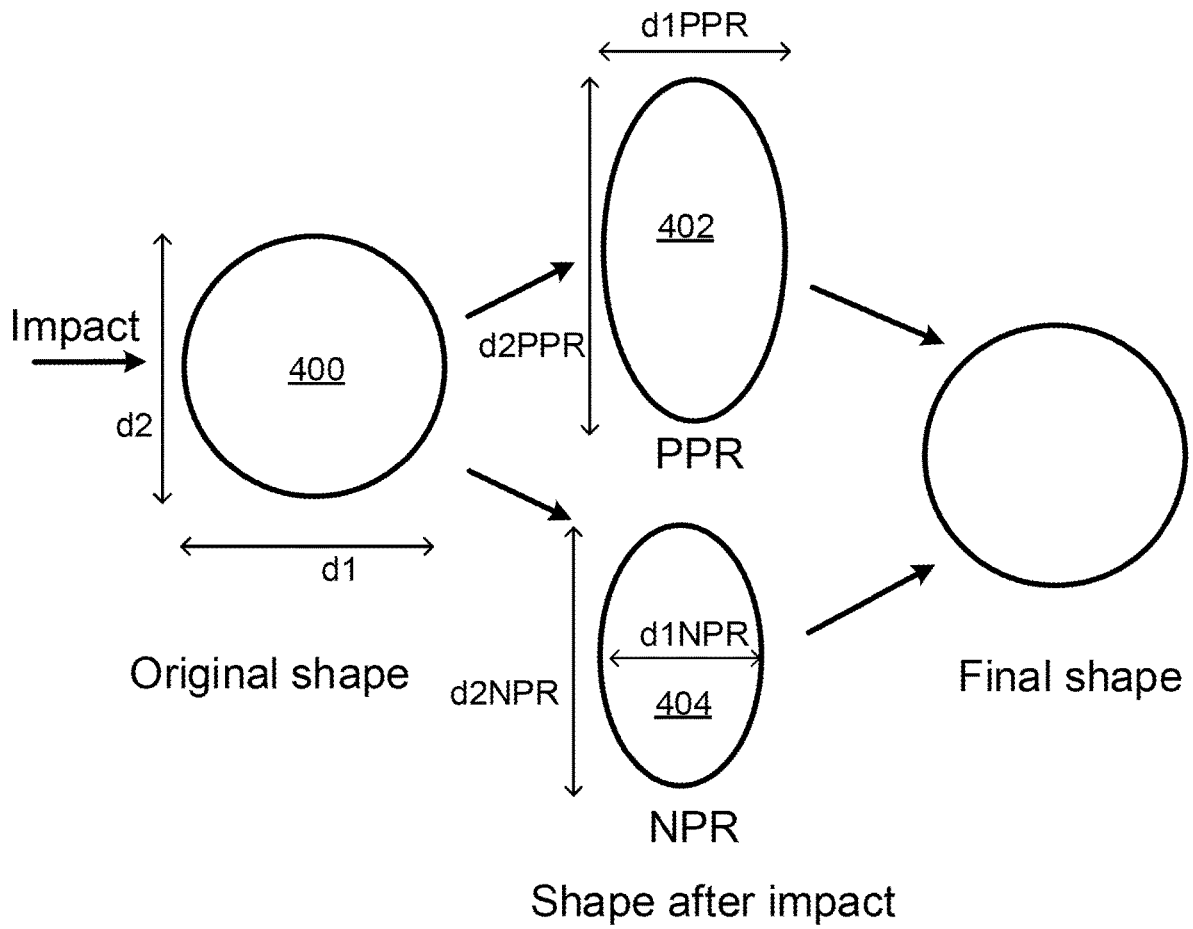
FIG. 4 is an illustration of balls with negative and positive Poisson's ratios.

FIG. 4 shows a schematic depiction of the change in diameter of a material 400 upon impact. Although the material 400 in FIG. 4 is shown as a rounded ball, a similar deformation occurs in materials of other shapes. Prior to impact, the material 400 has a diameter d1 in the direction of the impact and a diameter d2 in the direction perpendicular to the impact. If the material 400 is a PPR material, the material undergoes significant deformation (e.g., elastic deformation) into a shape 402, such that the diameter in the direction of the impact decreases to d1PPR and the diameter in the direction perpendicular to the impact increases to d2PPR. By contrast, if the material 400 is an NPR material, the material undergoes less extensive deformation into a shape 404. The diameter of the shape 404 in the direction of the impact decreases to d1NPR, which is approximately the same as d1PPR. However, the diameter of the shape 404 in the direction perpendicular to the impact also decrease, to d2NPR. The magnitude of the difference between d2 and d2NPR is less than the magnitude of the difference between d2 and d2PPR, meaning that the NPR material undergoes less deformation than the PPR ball. This reduction in total deformation that is achievable by an NPR material enables the NPR material to have a different (e.g., longer) launching distance than an otherwise comparable PPR material at least in part because the NPR material has a lower wind resistance due to its smaller diameter upon compression.

Figure 5A:
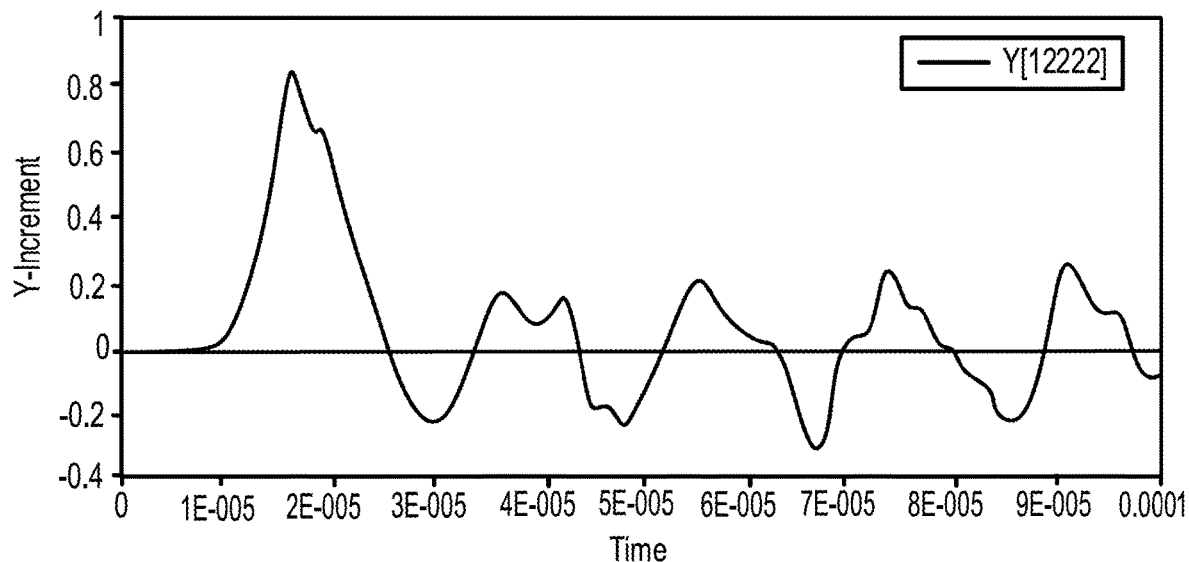
FIGS. 5A and 5B are plots of diameter versus time.
Figure 5B:
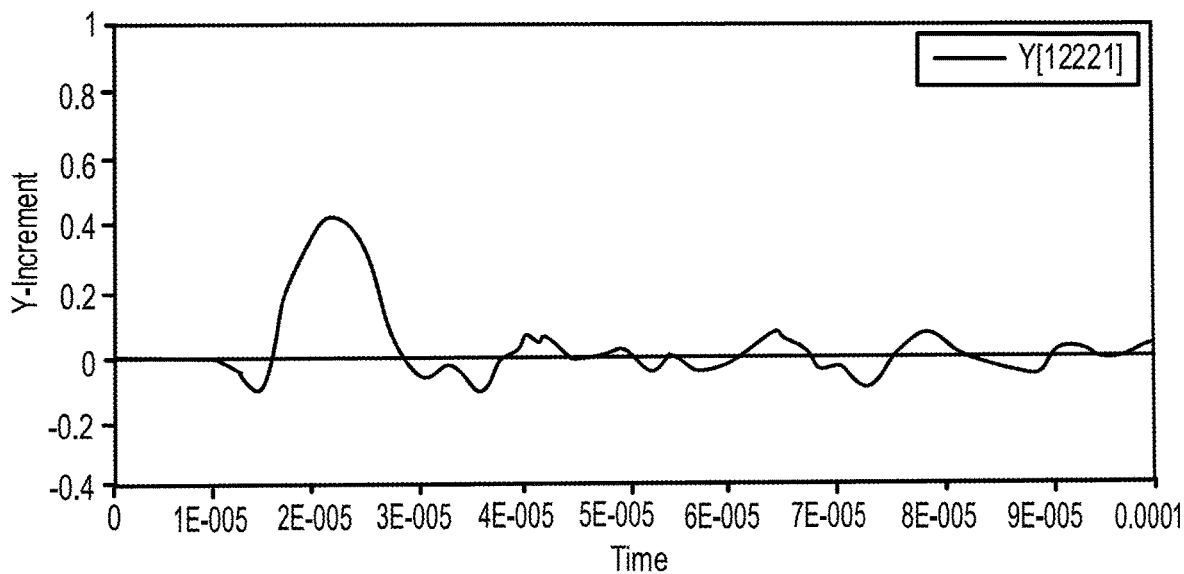

FIGS. 5A and 5B show plots of diameter versus time for a substantially spherical PPR material with a Poisson's ratio of 0.45 and an NPR material with a Poisson's ratio of −0.45, respectively, responsive to being struck with an equivalent force. In this example, the NPR material undergoes a smaller initial change in diameter than does the PPR material, and the oscillations in diameter are smaller in magnitude and dampen more quickly. Again, although FIGS. 5A and 5B are specific to substantially spherical materials, a similar behavior occurs in NPR and PPR materials of other shapes.

Figure 6:
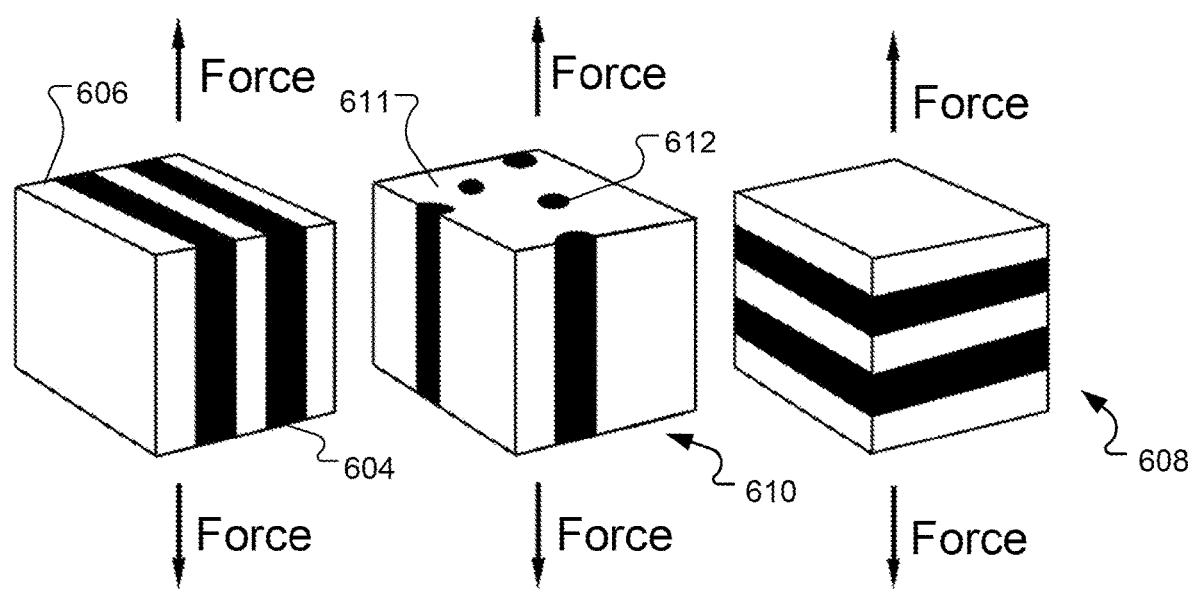
FIG. 6 is an illustration of composite materials.

FIG. 6 illustrates examples of NPR-PPR composite materials. An NPR-PPR composite material 602 is a laminar composite including alternating layers 604 of NPR material and layers 606 of PPR material. The layers 604, 606 are arranged in parallel to a force to be exerted on the composite material 602. Although the layers 604, 606 are shown as having equal width, in some examples, a laminar composite can have layers of different widths.

An NPR-PPR composite material 608 is a laminar composite including alternating layers of NPR material and PPR material, with the layers arranged perpendicular to a force to be exerted on the material 608. In some examples, the layers of a laminar composite are arranged at an angle to the expected force that is neither perpendicular nor parallel.

An NPR-PPR composite material 612 is a matrix composite including a matrix phase 611 of NPR material with a reinforcement phase 612 of PPR material. In the material 612, the reinforcement phase 612 includes fibers of the PPR material; in some examples, the reinforcement phase 612 can include particles or other configuration. In some examples, NPR-PPR composite materials can have a matrix phase of a PPR material with a reinforcement phase of an NPR material.

Figure 7:
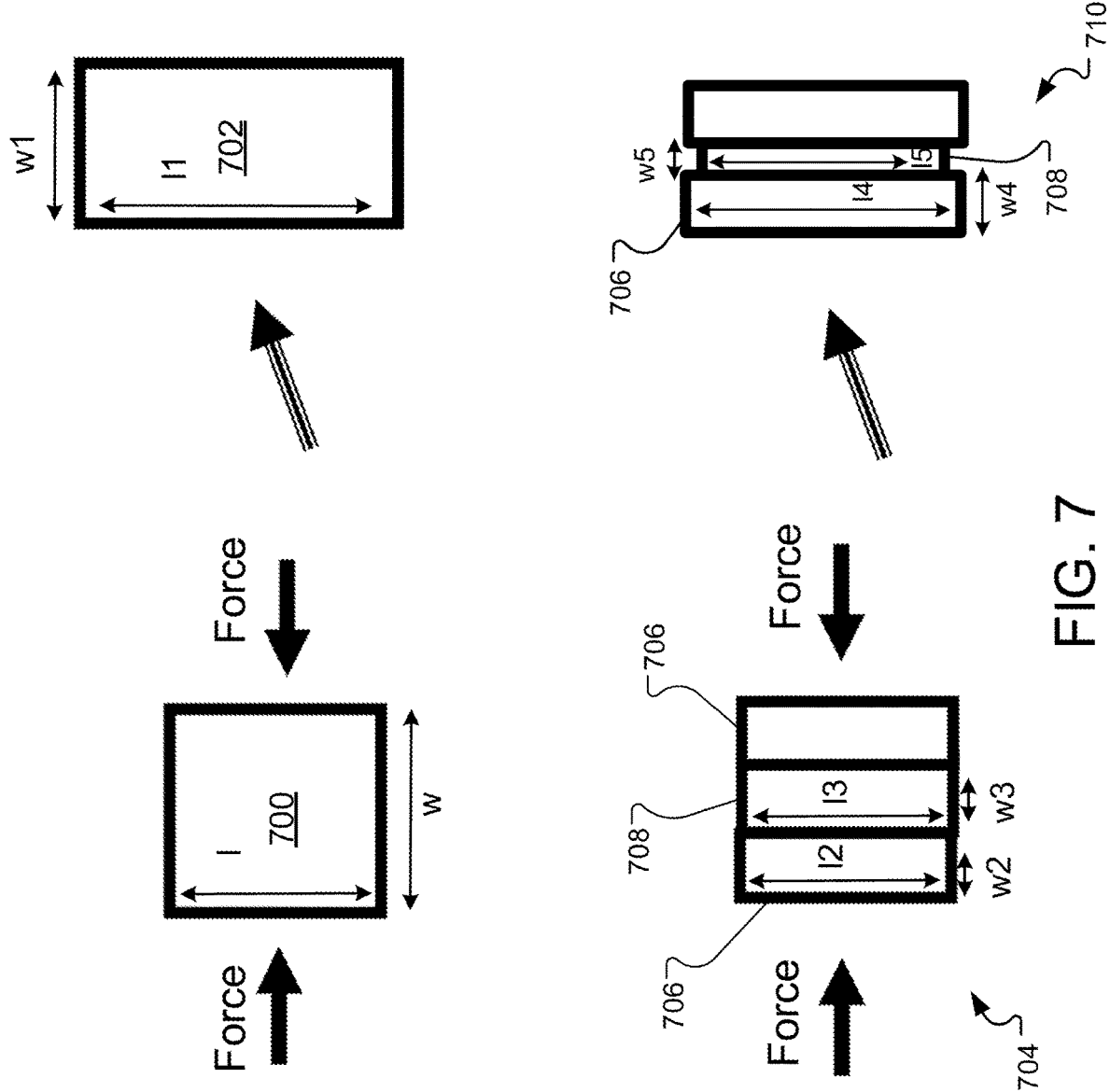
FIG. 7 is an illustration of a material with a positive Poisson's ratio and a composite material.

FIG. 7 illustrates the mechanical behavior of PPR and NPR/PPR composite materials. A hypothetical block 700 of PPR material, when compressed along its width w, deforms into a shape 702. The width w1 of the compressed block 702 is less than the width w of the uncompressed block 700, and the length l1 of the compressed block 702 is greater than the length l of the uncompressed block: the material compresses along the axis to which the compressive force is applied and expands along a perpendicular axis.

A block 704 of NPR/PPR composite material includes a region 708 of NPR material sandwiched between two regions 706 of PPR material. When the block 704 of composite material is compressed along its width, the material deforms into a shape 710. The PPR regions 706 compress along the axis of compression and expand along a perpendicular axis, e.g., as described above for the block 700 of PPR material, such that, e.g., the width w2 of a region 706 of uncompressed PPR material compresses to a smaller width w4 and the length l2 of the region 706 expands to a greater length l4. In contrast, the NPR region 708 compresses along both the axis of compression and along the perpendicular axis, such that, e.g., both the width w3 and length l3 of the uncompressed NPR region 708 are greater than the width w5 and length l5 of the compressed NPR region 708.

Figure 8:
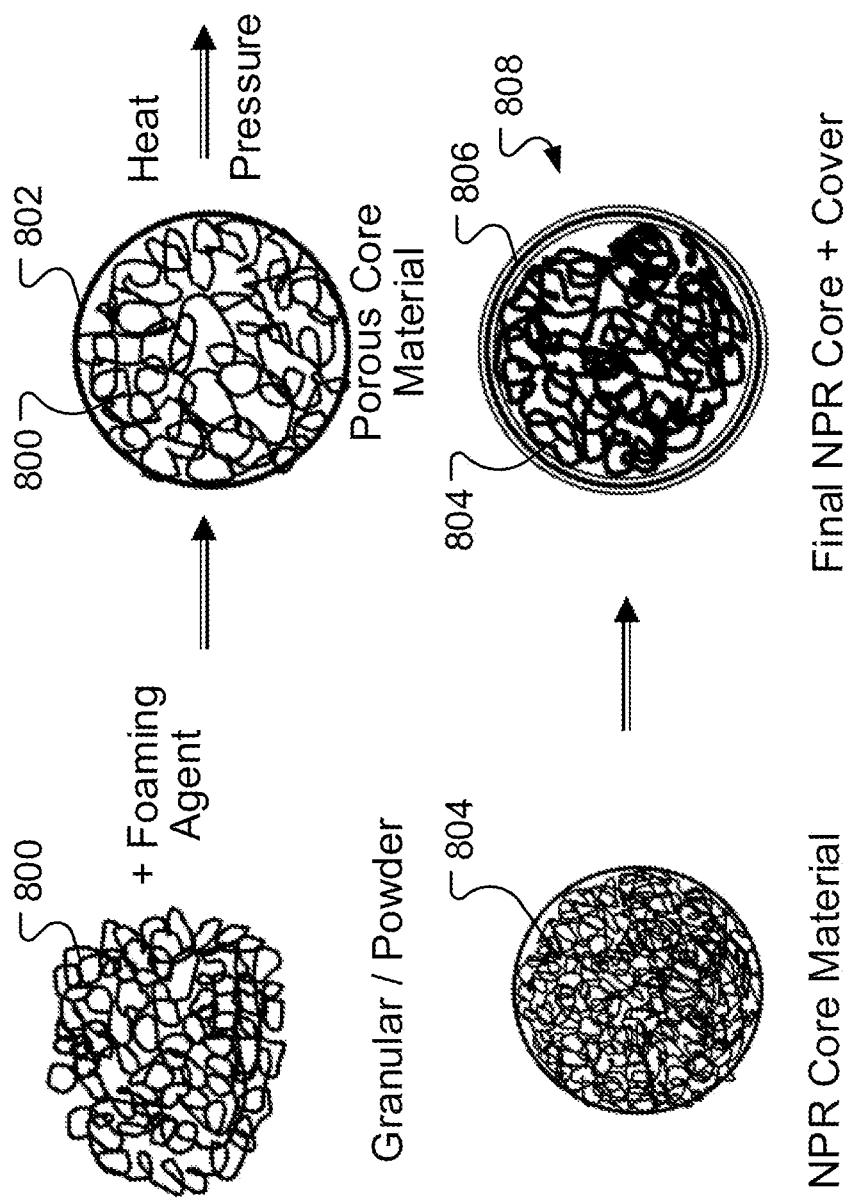
FIG. 8 is a diagram of a method of making an NPR material.

FIG. 8 illustrates an example method of making an object, such as an intraocular lens, formed of an NPR material. A granular or powdered material, such as a polymer material (e.g., a rubber) is mixed with a foaming agent to form a porous material 800. The porous material 800 is placed into a mold 802. Pressure is applied to compress the material 800 and the compressed material is heated to a temperature above its softening point. The material is then allowed to cool, resulting in an NPR foam 804. The NPR foam 804 is covered with an outer layer 806, such as a polymer layer, and heat and pressure is applied again to cure the final material into an object 808.

FIGS. 9A-9F show embodiments of intraocular lenses that include a negative Poisson's ratio (NPR) material for the circumferential optic, each individual haptics, or any combination thereof. In the IOLs depicted in FIGS. 9A-9F, the materials used to form the optical zone include a transparent polymer material having a positive Poisson's ratio (PPR) with a first index of refraction. The materials used to form the optical zone can include acrylic (e.g., polymethylmethacrylate), polycarbonate, silicone (e.g., silicone rubber), or hydrogel. One or more of the haptics, the circumferential optic, or all can be formed of a material having a negative Poisson's ration (NPR) with a second index of refraction different from the first index of refraction. For instance, the haptics, the circumferential optic, or combinations thereof can incorporate NPR materials of acrylics (e.g., PMMA), silicone, polycarbonate, or hydrogels. In the IOLs illustrated in FIGS. 9A-9F, the surfaces of the optical zone can be convex or planar.

Figure 9A:
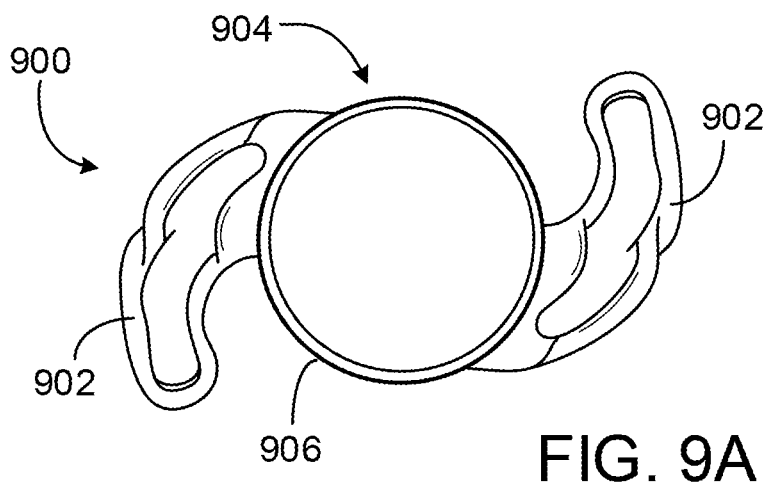
FIGS. 9A-9F are illustrations of intraocular lenses.

FIG. 9A shows a two-loop haptic embodiment 900 having two closed-loop haptics 902. Each haptic 902 extends outwardly from the outer edge of a circumferential optic 906 of an optic 904, and returns to be attached at the circumferential optic 906 to form a closed loop haptic structure. The two haptics 902 are at diametrically opposed positions around the circumference of the optic. Each haptic 902 is significantly smaller in width than the optic 904. The circumferential optic 906, one or more closed-loop haptics 902, or all can be made of NPR material.

Figure 9B:
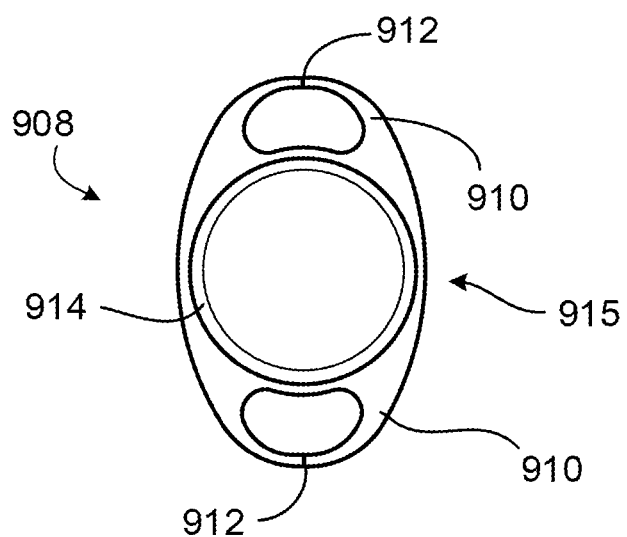

FIG. 9B shows an iris claw IOL 908. The iris claw IOL 908 includes two oval haptics 910, each of which is split in a middle 912 to form a pincer/claw-like structure. The two haptics 910 are attached to a circumferential optic 914 and disposed at diametrically opposed positions around a circumference of an optic 915. One or more of the oval haptics 910, the circumferential optic 914, or all can be made of NPR material.

Figure 9C:
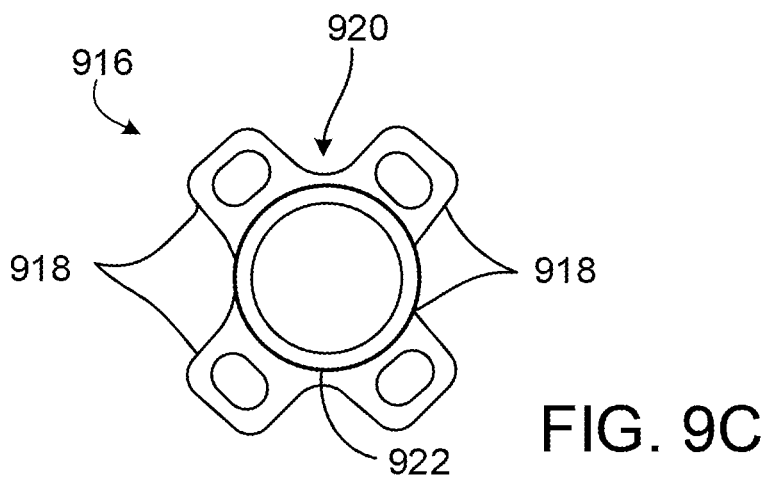

FIG. 9C shows a four plate-loop IOL 916 having two haptics 918. Each haptic 918 has a width approximately equal to the diameter of an optic 920. The four plate-loop haptics are disposed at evenly spaced intervals around a circumference of the optic 920 and attached to the optic 920 at the circumferential optic 922. One or more of the plate-loop haptics 918, the circumferential optic 922, or all can be made of NPR material.

Figure 9D:
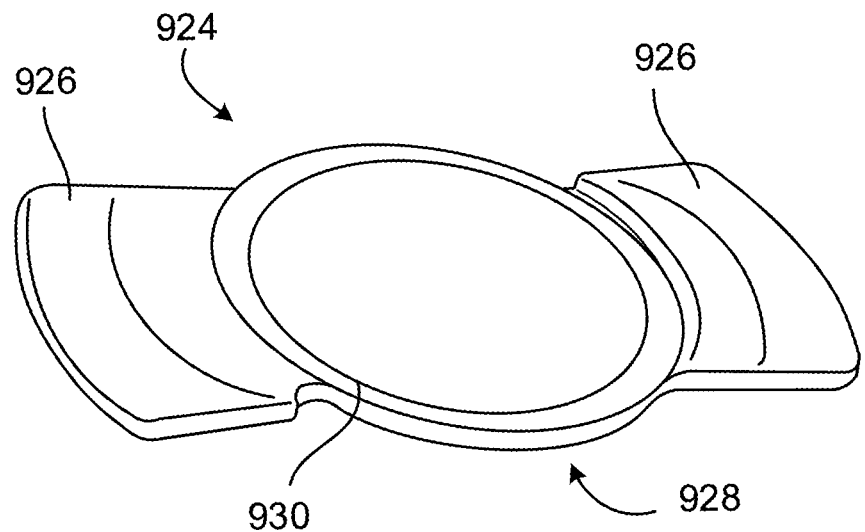

FIG. 9D shows a solid plate IOL 924 having solid plate haptics 926. Each solid plate haptic 926 has a width substantially equal to the diameter of an optic 928. The two solid plate haptics 926 are disposed at diametrically opposed positions around a circumference of the optic 9288 and attached to the optic 928 at a circumferential optic 930. One or more of the solid plate haptics 926, the circumferential optic 930, or all can be made of NPR material.

Figure 9E:
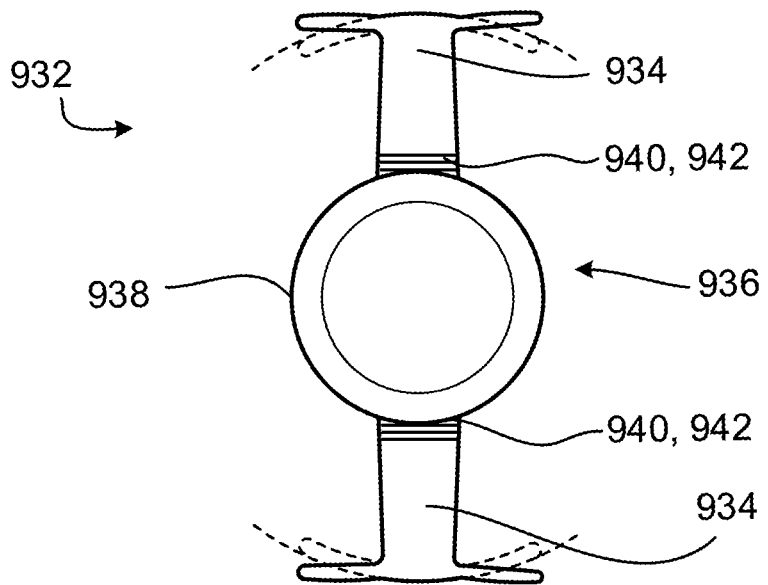

FIG. 9E shows a T-shaped haptic IOL 932 having T-shaped haptics 934. The T-shaped haptics 934 are disposed at diametrically opposed positions around a circumference of an optic 936 and attached to the optic 936 at the circumferential optic 938 by respective hinges 934 that include grooves 942 in the haptic. One or more of the T-shaped haptics 934, a circumferential optic 938, or all can be formed of NPR material.

Figure 9F:
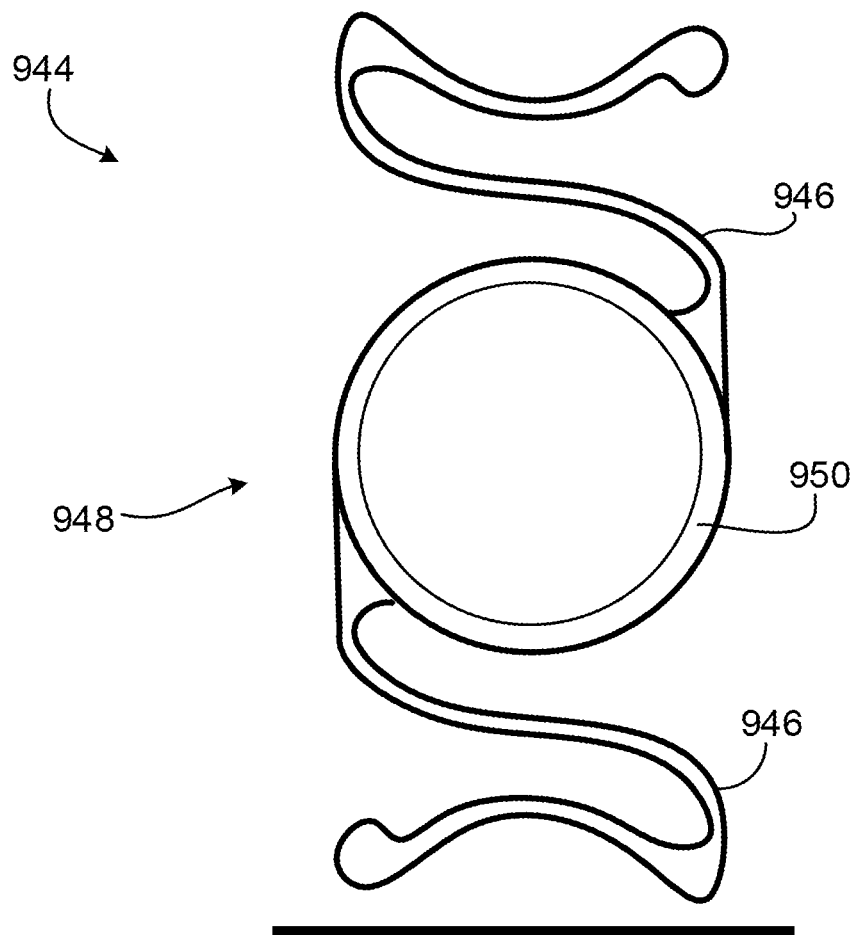

FIG. 9F shows an S-shaped haptic IOL 944 that includes two-loop haptics 946. The two-loop haptics 946 are disposed at diametrically opposed positions around the circumference of an optic 948 and attached to the optic 948 at a circumferential optic 950. Each two-loop haptics 946 includes an S-shape and has a width that is substantially less than a diameter of the optic 948. One or more of the haptics 946, the circumferential optic 950, or all can be formed of an NPR material.

Other designs of the intraocular lens including different numbers and shapes of the haptics and radii of curvature of the optic surfaces are within the scope of this disclosure.

Figure 10:
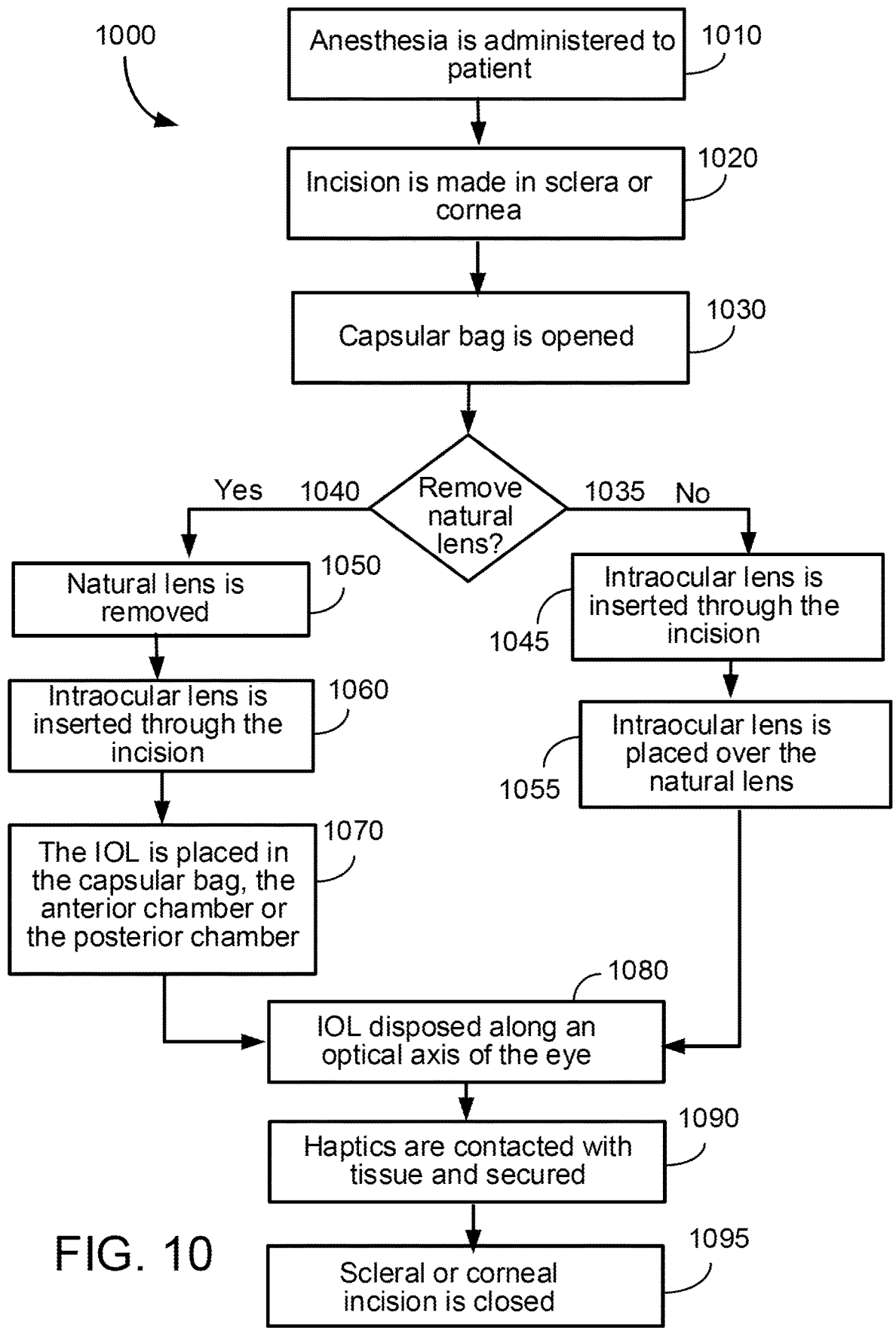
FIG. 10 is a flow chart.

FIG. 10 is a flow chart of an example process (1000) for implantation of an intraocular lens into an eye using surgical intervention. The surgery includes administering to the patient regional anesthesia, sedative anesthesia, or both (1010). A small incision is made in the sclera adjacent to the cornea or within the cornea (1020). The capsular bag is opened (1030). The natural lens may be removed from the eye (1040, 1050) or it may be retained in the eye (1035). The IOL is inserted into the eye through the incision (1045, 1060). The IOL may be positioned in place of the removed natural lens (1070), or it may be placed over the retained natural lens (1055), e.g., using one or more of the following techniques: insertion of a rigid IOL using a forceps; insertion of a folded, flexible IOL using a folding forceps, injection of a folded, flexible IOL using an injector loaded with the IOL, or another suitable technique. The IOL may be placed in the capsular bag, the anterior chamber, or the posterior chamber (1070). The IOL is disposed along an optical axis of the eye (1080) and one or more of the haptics are placed in contact with the tissue of the eye (1090). This tissue in contact with the haptics may include the capsular bag, the iris, the ciliary sulcus, the sclera, or a combination of these (1090). In some cases the IOL can be secured by positioning of the haptics without the need for further attachment. In some cases the haptics are further fastened using sutures, glue, or another suitable attachment mechanism, or a combination of these (1090). The incision in the sclera or the cornea is closed using fixation sutures, glue, cauterization, or another suitable closure mechanism, or a combination of these (1095).

Other embodiments are within the scope of the following claims.

What is claimed is:

1. An intraocular lens comprising:
   a substantially circular lens element formed of a transparent material, in which the lens element comprises:
      an inner region formed of a polymer material having a positive Poisson's ratio, the inner region having a first index of refraction; and
      an outer region disposed circumferentially surrounding the inner region, the outer region formed of a polymer foam material having a negative Poisson's ratio, the outer region having a second index of refraction different from the first index of refraction; and
   one or more haptics extending outwardly from an outer edge of the lens element, the entirety of each of the one or more haptics formed of a polymer foam material having a negative Poisson's ratio (NPR), in which the one or more haptics are configured to couple the intraocular lens to an eye of a patient.

2. The intraocular lens of claim 1, in which the inner region of the lens element is formed of acrylic, silicone, or hydrogel.

3. The intraocular lens of claim 1, comprising two haptics disposed at diametrically opposed positions around a circumference of the lens element.

4. The intraocular lens of claim 1, comprising four haptics disposed at evenly spaced intervals around a circumference of the lens element.

5. The intraocular lens of claim 1, in which the one or more haptics each comprises a loop haptic.

6. The intraocular lens of claim 1, in which the one or more haptics each comprises a plate loop haptic.

7. The intraocular lens of claim 1, in which the one or more haptics each comprises a solid plate haptic.

8. The intraocular lens of claim 1, in which the one or more haptics each comprises a T-shaped haptic.

9. The intraocular lens of claim 1, in which a width of each of the haptics is less than a diameter of the lens element.

10. The intraocular lens of claim 1, in which a width of each of the haptics is substantially equal to a diameter of the lens element.

11. The intraocular lens of claim 1, in which each of the one or more haptics comprises a hinge attaching the haptic to the lens element.

12. The intraocular lens of claim 11, in which the hinge comprises grooves in the haptic.

13. The intraocular lens of claim 1, in which the lens element is convex.

14. The intraocular lens of claim 1, in which the polymer foam material of the outer region of the lens element is composed of a cellular structure having a characteristic dimension of between 0.1 µm and 3 µm.

15. The intraocular lens of claim 1, in which the polymer foam material of the outer region of the lens element comprises a foam of acrylic, silicone, or hydrogel.

16. The intraocular lens of claim 1, in which the polymer foam material of the outer region of the lens element comprises a re-entrant foam structure.

17. The intraocular lens of claim 1, in which the polymer foam material of the one or more haptics comprises a re-entrant foam structure.

18. The intraocular lens of claim 1, in which the polymer foam material of the one or more haptics is composed of a cellular structure having a characteristic dimension of between 0.1 µm and 3 µm.

\* \* \* \* \*